(12) United States Patent
Banauch et al.

(10) Patent No.: US 6,383,453 B1
(45) Date of Patent: May 7, 2002

(54) MULTI-ALIQUOT STORAGE VESSEL AND BREAK TOOL

(76) Inventors: Inge Banauch, Kaspar Kerll Strasse 19, D-81245 Munich (DE); Hans G. Kloepfer, 2410 Hawthorn Pl., Noblesville, IN (US) 46060

( * ) Notice: Subject to any disclaimer, the term of this patent is extended or adjusted under 35 U.S.C. 154(b) by 0 days.

(21) Appl. No.: 09/436,578

(22) Filed: Nov. 9, 1999

(51) Int. Cl.$^7$ ................................................ B01L 3/00
(52) U.S. Cl. ........................ 422/102; 422/104; 220/326
(58) Field of Search ................................ 422/102, 913, 422/104; 435/288.2, 288.1; 220/4.07, 4.06, 4.26, 4.04, 692, 326, 4.27; D24/224, 226; 215/6; 206/828, 569

(56) References Cited

U.S. PATENT DOCUMENTS

| | | | |
|---|---|---|---|
| 3,701,434 A | * | 10/1972 | Moore |
| 3,825,410 A | * | 7/1974 | Bagshawe |
| 4,272,478 A | * | 6/1981 | Vihko |
| 5,409,117 A | * | 4/1995 | Meador |
| 5,516,490 A | * | 5/1996 | Sanadi |
| 5,916,527 A | * | 6/1999 | Haswell |

* cited by examiner

Primary Examiner—Joseph W. Drodge
Assistant Examiner—Terry K. Cecil
(74) Attorney, Agent, or Firm—E. Victor Indiano

(57) ABSTRACT

A multi-aliquot storage vessel including a container having an upper end and a lower end. At least one of the upper and lower ends is an open end. The length of the container between the upper and lower ends is divided into a plurality of aliquots, wherein a breakpoint is formed between each two of the plurality of aliquots. The container can be broken along these breakpoints through the application of a separating force, to divide the container into subunits containing one or more aliquots. A cap is formed to be attachable to an open end of the container. A sealing device seals the junction between the cap and the open end of the container. A break tool for facilitating the division of the container is also disclosed. The break tool includes upper and lower components, the proximal ends of which pivotably rotate about a hinge between an open position and a closed position. The distal end of the upper and lower components have upper and lower container receiving portions, respectively, which form a container insertion port in which the container can be inserted when the break tool is in the open position and in which the container can be held when the break tool is in the closed position.

21 Claims, 4 Drawing Sheets

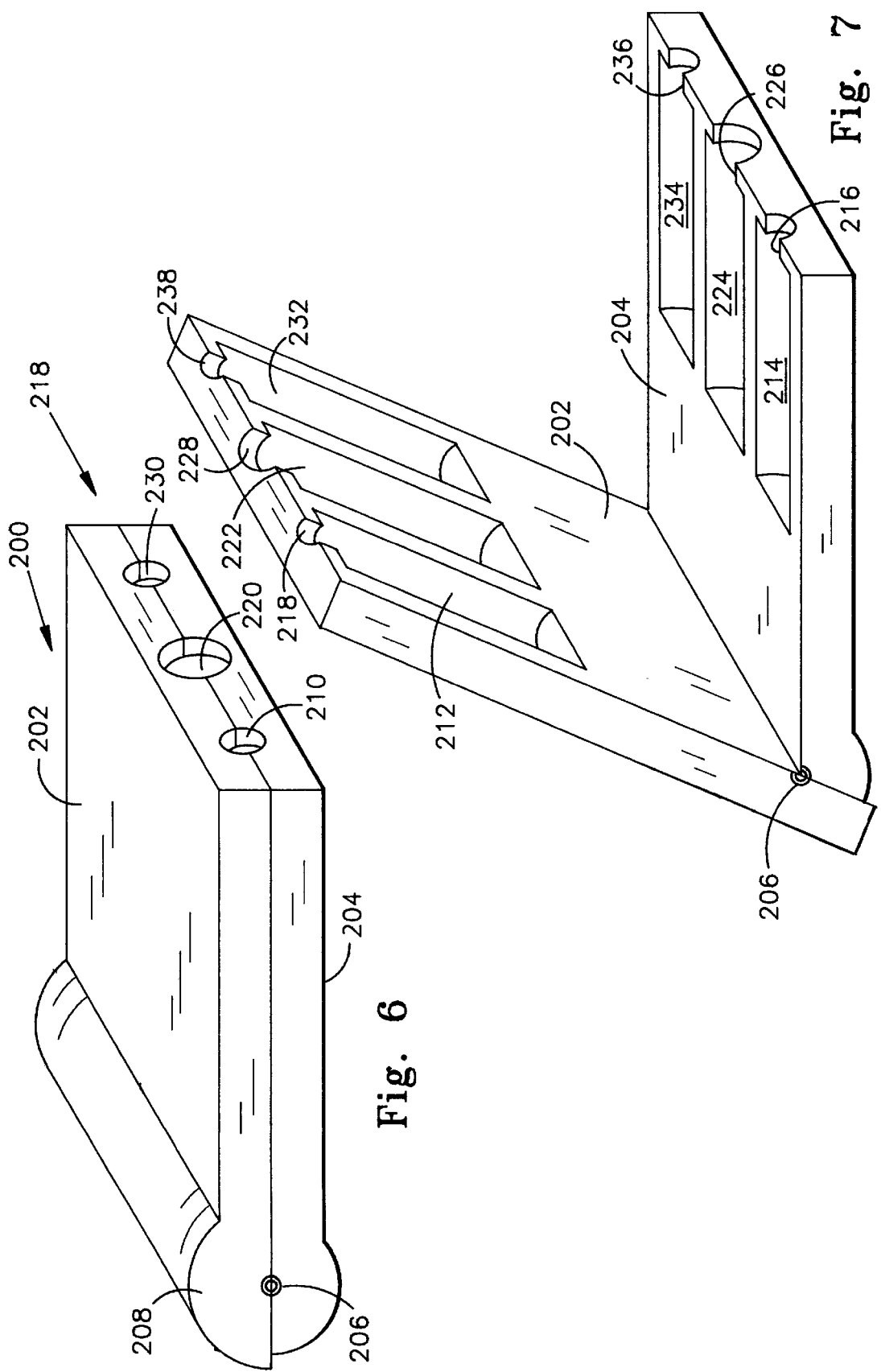

MULTI-ALIQUOT STORAGE VESSEL AND BREAK TOOL

FIELD OF THE INVENTION

This invention relates to a storage container for storing, freezing and apportioning specimens. More particularly, the invention relates to a storage container for the freezing and storage of collected samples and a break tool that can be used for dividing the storage container and sample, the storage container having breakpoints at which the container and frozen sample can be divided without the need of thawing and refreezing the remainder of the samples.

BACKGROUND OF THE INVENTION

Unstable fluids and other substances in solution can often be effectively stabilized by freezing. A sample of the frozen fluid will remain stable for extended periods as long as it is kept in the frozen state. Frequently these fluids are collected in relatively large quantities, ("collected samples"), and are used in smaller quantities, ("specimens"), over an extended period of time.

When a specimen is needed, it often requires thawing the entire collected sample to obtain the specimen currently needed, and then refreezing the remainder of the collected sample. However, frequent freezing and thawing cycles are almost always detrimental to the unstable ingredients in the collected sample.

One solution is to store the collected sample in multiple small individual vessels. Then, when a specimen is needed, the necessary number of individual vessels can be thawed to provide the specimen without having to thaw and refreeze the entire collected sample. However, separation and freezing in separate vessels is often cumbersome and requires a large amount of disposable containers and freezer capacity in order to store all of the individual specimen vessels. Having a large number of individual specimen vessels also increases the chance of confusion and mix-up of the stored specimens.

Accordingly, a need exists for an apparatus for storing and freezing collected samples that does not require storing the collected sample in a large number of individual vessels, and also, when a specimen is needed, does not require thawing the entire collected sample and refreezing the unneeded portion.

SUMMARY OF THE INVENTION

In accordance with the present invention, a multi-aliquot storage vessel is provided for the freezing and storage of collected samples. The multi-aliquot storage vessel can be divided while its contents remain frozen and the divided portions can be resealed for further storage or used as needed. The division is accomplished by the controlled breakage of the multi-aliquot storage vessel at predetermined breaking points.

A multi-aliquot storage vessel includes a container, at least one cap and a sealing means. The container has an upper end and a lower end, at least one of which is an open end. The length of the container between the upper end and the lower end is divided into a plurality of aliquots. A breakpoint is formed between each pair of aliquots at which the container can be divided. A break tool can be used to divide the container at the desired breakpoint. A separable cap is formed to cover the open end of the container. The sealing means forms a seal between the cap and the container.

In one embodiment, the sealing means is a clamp which is attached to the container and the cap when the container has one open end, and is attached to both caps if the container has two open ends.

In an alternative embodiment, the sealing means includes screw threads on each aliquot of the container and mating screw threads on each cap. An open end of the container is sealed by screwing the cap onto the open end of the container.

A feature of the present invention is that a frozen sample can be divided into smaller quantities without the need of thawing the entire sample. The container includes multiple breakpoints at which the container can be divided along with its contents. One or more of the divided portions can be thawed and used. The remaining portions can be stored or transported to another site for processing and testing without having to be thawed and refrozen.

Another feature of the present invention is that a sample, when collected, can be placed into a single container, frozen and stored in a freezer for later usage in smaller quantities, each smaller quantity being accessible without the need of thawing the entire sample.

Additional objects, advantages and novel features of the invention are set forth in the description that follows, and will become apparent to those skilled in the art upon reviewing the drawings in connection with the following description.

BRIEF DESCRIPTION OF THE DRAWINGS

FIG. 6 shows a break tool in the closed position;

FIG. 7 shows a break tool in the open position; and

DETAILED DESCRIPTION OF THE PREFERRED EMBODIMENT OF THE INVENTION

Figure 1:
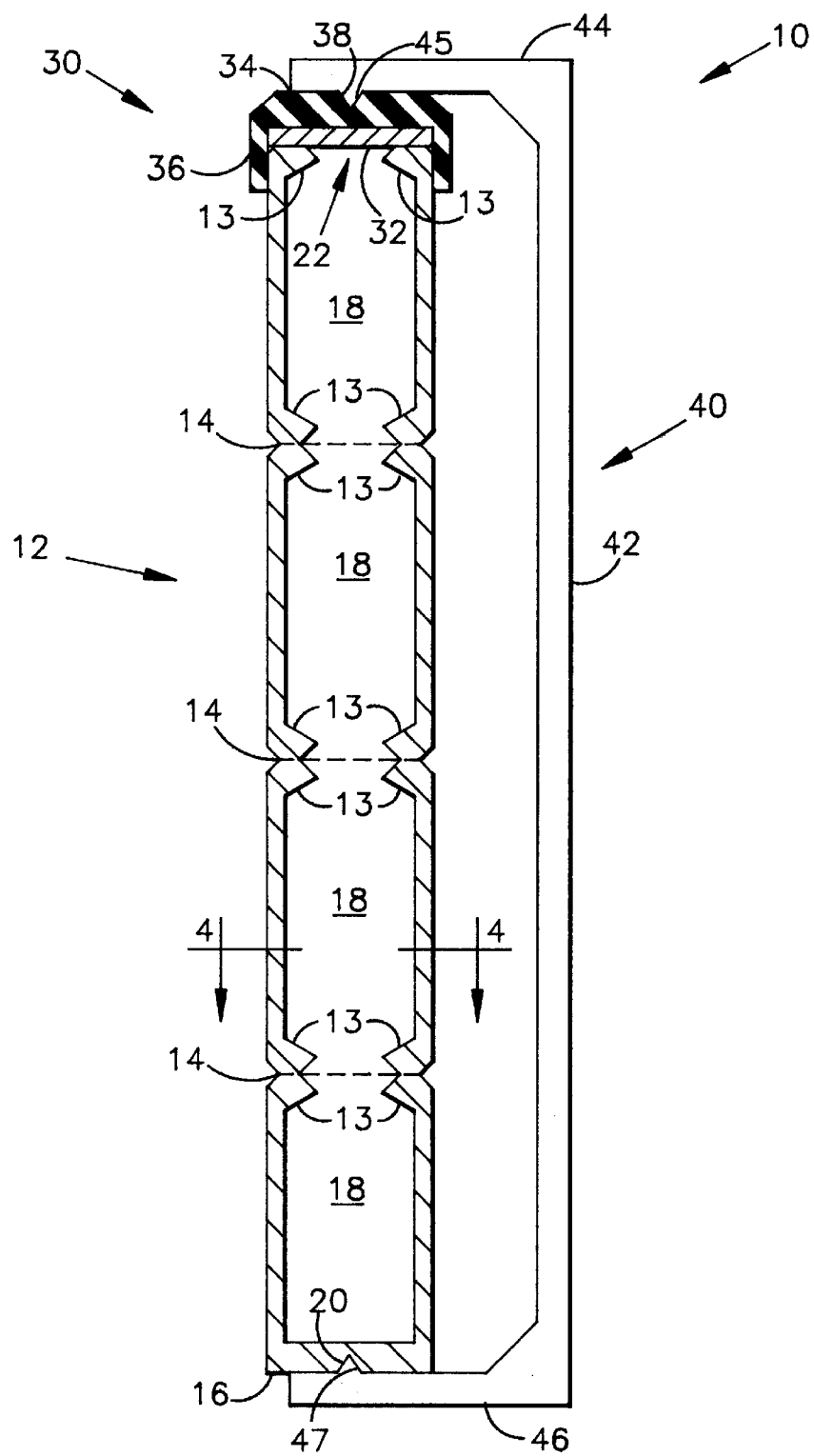
FIG. 1 shows a side, sectional view of an aliquot storage vessel with a C-shaped clamp.

FIG. 1 shows an aliquot storage vessel 10 according to one embodiment of the present invention. The aliquot storage vessel 10 includes a cylindrical multi-aliquot container 12, a cap 30 and a clamp 40. In this embodiment, the tension of the clamp 40 is used to maintain a vapor tight seal between the cap 30 and the multi-aliquot container 12. It is readily apparent that a clamp can have various shapes to provide the desired vapor-tight seal between the container 12 and the cap 30.

The multi-aliquot container 12 has a closed bottom end 16 and an open top end 22. A plurality of breakpoints 14 are formed along the length of the multi-aliquot container 12 between the bottom end 16 and the open top end 22. The breakpoints 14 comprise formed, ring-shaped "notches" that extend around the perimeter of the multi-aliquot container 12, and separate the multi-aliquot container 12 into individual aliquots 18 which can be separated from the remainder of the sample as needed. The interior of the breakpoint 14 has protrusions 13 which contribute to breakage at the breakpoint 14 and also prevent the frozen sample in the aliquots 18 from sliding when the container 12 is broken at the breakpoint 14.

The breakpoints 14 are designed to facilitate breakage of the container 12 at the breakpoint 14 since they comprise reduced thickness areas of the container 12 with inwardly directed protrusions on both the interior of exterior of the container 12 at the breakpoint 14. The multi-aliquot container 12 is designed so that a radially directed gentle manual force will break the multi-aliquot container 12 and the frozen sample inside the multi-aliquot container 12 at the breakpoint 14 around which the gentle manual force is applied, leaving a generally flat surface on the end of each portion formerly connected at the breakpoint 14. The bottom 16 of the multi-aliquot container 12 includes a centrally disposed depression or cavity 20 which extends partly (but not completely) through the bottom 16.

The cap 30 includes a top surface 34, an axially extending perimetral lip 36 and a sealing member 32. The top surface 34 is generally planar, but includes a centrally disposed depression or cavity 38. The perimetral lip 36 extends axially from the perimeter of the radially extending top surface 34 away from the face of the top surface 34 having the cavity 38.

The sealing member 32 is generally disk-shaped and planar, and is attached to the lower face of the top surface 34 and is sandwiched between the upper rim of the container 12 and the radially extending lower axially facing surface of the top surface 34 of the cap 30. The perimeter of the sealing member 32 is surrounded by the perimetral lip 36. When the cap 30 is attached to the multi-aliquot container 12, the top surface 34 of the cap 30 covers the open-end 22 of the multi-aliquot container 12; the perimetral lip 36 of the cap 30 surrounds the perimeter of the multi-aliquot container 12 near the open end 22; the face of the top surface 34 with the cavity 38 faces away from the multi-aliquot container 12; and the sealing member 32 contacts the top edge of the open end 22 of the multi-aliquot container 12. The sealing member 32 of the cap 30 is made of a soft elastomeric material (such as a soft gasket material) that conforms to the rim of the open end 22 to form an vapor tight seal therebetween. The sealing member 32 provides a vapor tight seal of the stored and frozen specimen even when the top of the frozen specimen includes ridges due to a prior separation of an aliquot 18 from the multi-aliquot container 12.

The clamp 40 is generally C-shaped. The clamp 40 includes an axially extending center section 42 and a radially extending upper arm 44 having an axially inwardly extending top protrusion 45. The clamp 40 further includes a radially extending lower arm 46 having an axially inwardly extending protrusion 47. The upper and lower arms 44, 46 have an axially inwardly directed bias towards one another such that the clamp 40 provides a compressive force holding the cap 30 and the sealing member 32 against the multi-aliquot container 12. The clamp 40 is attached to the multi-aliquot container 12 after the cap 30 has been placed over the open end 22. The top protrusion 45 is inserted into the cavity 38 of the cap 30 and the bottom protrusion 47 is inserted into the cavity 20 on the bottom 16 of the multi-aliquot container 12. The compressive force exerted by the axially inwardly directed bias of the upper and lower arms 44, 46 compresses the sealing member 32 of the cap 30 to form a vapor tight seal at the open end 22 of the multi-aliquot container 12.

Figure 2:
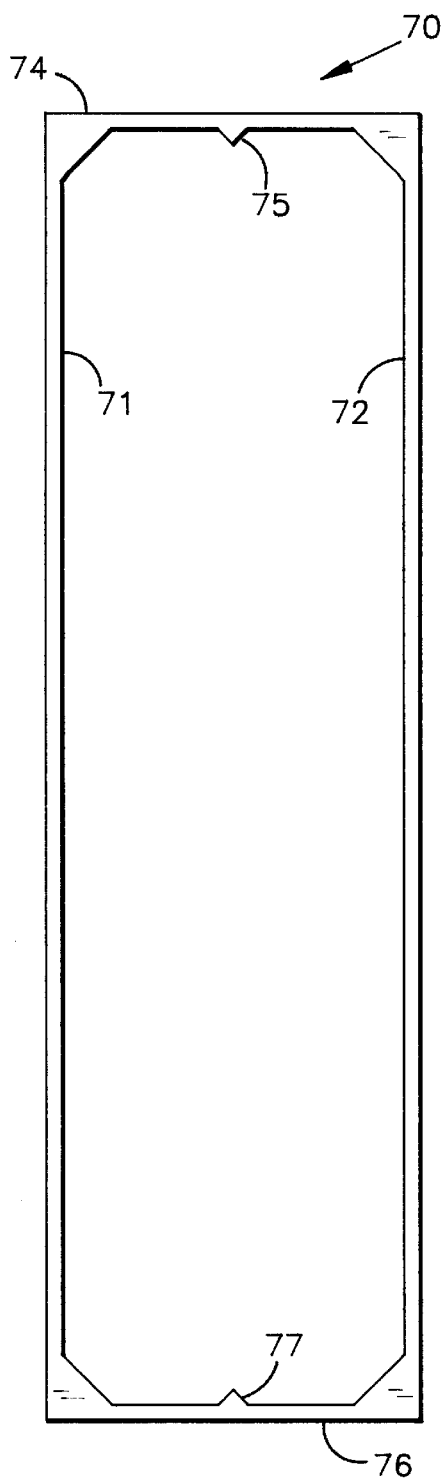
FIG. 2 shows a side view of an O-shaped clamp for a four aliquot vessel.

An alternative embodiment of a clamp 70, shown in FIG. 2, is generally O-shaped. The clamp 70 is also designed to be used with the cap 30 and multi-aliquot container 12 shown in FIG. 1. The clamp 70 includes axially extending center sections 71, 72; a radially extending upper arm 74, and a radially extending lower arm 76. The radially extending upper arm 74 has an axially inwardly extending top protrusion 75. The radially extending lower arm 76 has an axially inwardly extending protrusion 77. The upper and lower arms 74, 76 have an axially inwardly directed bias towards one another such that the clamp 70 provides a compressive force holding the cap 30 and the sealing member 32 against the multi-aliquot container 12. The clamp 70 is attached to the multi-aliquot container 12 after the cap 30 has been placed over the open end 22. The top protrusion 75 is inserted into the cavity 38 of the cap 30 and the bottom protrusion 77 is inserted into the cavity 20 on the bottom 16 of the multi-aliquot container 12. The compressive force exerted by the axially inwardly directed bias of the upper and lower arms 74, 76 compresses the sealing member 32 of the cap 30 to form a vapor tight seal at the open end 22 of the multi-aliquot container 12.

Figure 3:
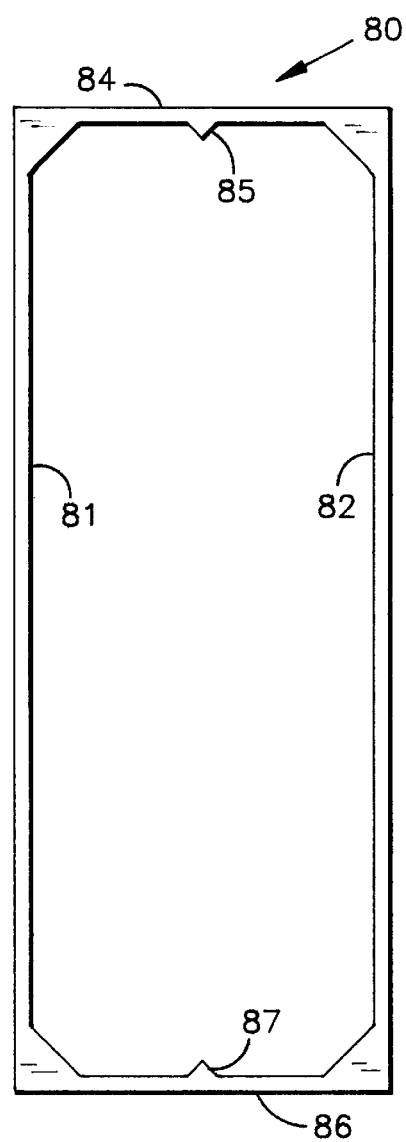
FIG. 3 shows a side view of an O-shaped clamp for a three aliquot vessel.

A clamp 80, shown in FIG. 3, is also generally O-shaped and is sized to be used with a three aliquot container. The clamp 80 is designed to be used with the cap 30 and multi-aliquot container 12 shown in FIG. 1 after one of the aliquots 18 has been separated. The clamp 80 includes axially extending center sections 81, 82; a radially extending upper arm 84, and a radially extending lower arm 86. The radially extending upper arm 84 has an axially inwardly extending top protrusion 85. The radially extending lower arm 86 has an axially inwardly extending protrusion 87. The upper and lower arms 84, 86 have an axially inwardly directed bias towards one another such that the clamp 80 provides a compressive force holding the cap 30 and the sealing member 32 against the multi-aliquot container 12. The clamp 80 is attached to the multi-aliquot container 12 after the cap 30 has been placed over the open end 22. The top protrusion 85 is inserted into the cavity 38 of the cap 30 and the bottom protrusion 87 is inserted into the cavity 20 on the bottom 16 of the multi-aliquot container 12. The compressive force exerted by the axially inwardly directed bias of the upper and lower arms 84, 86 compresses the sealing member 32 of the cap 30 to form a vapor tight seal at the open end 22 of the multi-aliquot container 12.

The multi-aliquot container 12, the cap 30 and the clamp should all be made of materials that can withstand deep freezing. Some preferred materials include polypropylene, polystyrene or polycarbonate plastic. The volume and number of aliquots 18 per multi-aliquot storage vessel 10 basically has no limitation. However, it has been found that five aliquot vessels 10 with total volumes of 2.5 to 20 milliliters (0.5–4.0 ml/aliquot) are preferred for clinical and chemical use.

The multi-aliquot storage vessel 10 is designed such that when the multi-aliquot container 12 is divided in a manner that leaves both the top and bottom ends open, a cap 30 can be attached to both the top and bottom ends of the multi-aliquot container 12. In this case, a first cap 30 is applied to the top open end of the multi-aliquot container 12 and a second cap 30 is applied to the bottom open end of the multi-aliquot container 12. The clamp 40 is applied such that the top protrusion 45 is inserted into the cavity 38 of the first cap 30 and the bottom protrusion 47 is inserted into the cavity 38 of the second cap 30. The compressive force exerted by the axially inwardly directed bias of the upper and lower arms 44, 46 compresses the sealing members 32 of both the first and second caps 30 to form a vapor tight seal at both the top and bottom open ends of the multi-aliquot container 12.

The plurality of breakpoints 14 divide the multi-aliquot container 12 into a plurality of aliquots 18. The vessel of FIG. 1 is shown with four aliquots 18. However a multi-aliquot container according to the present invention could be divided into more or less aliquots 18 as the particular application or convenience requires. Each aliquot 18 is defined by either: (1) two breakpoints 14 (middle aliquot); (2) a breakpoint 14 and an open end of the multi-aliquot container 12 (top or bottom aliquot); or (3) a breakpoint 14 and the bottom 16 of the multi-aliquot container 12 (bottom aliquot).

The clamp of the multi-aliquot storage vessel 10 is sized to create the necessary compressive force to maintain a vapor tight seal between the at least one cap 30 and the multi-aliquot container 12. FIG. 1 shows the clamp 40 sized for clamping a multi-aliquot container 12 having four aliquots 18. FIG. 2 shows another embodiment, the clamp 70, sized for clamping a multi-aliquot container 12 having four aliquots 18. FIG. 3 shows a clamp 80 sized for a multi-aliquot container 12 with three aliquots 18. A clamp can be designed for a multi-aliquot container 12 having any number of aliquots 18. The center portion of the appropriate clamp is sized, configured, and is made from a material that is designed to provide the upper arm and lower arm with the necessary compressive force to maintain a vapor-tight seal between the at least one cap 30 and the multi-aliquot container 12.

Instead of the fixed length clamps 40, 70, 80 shown in the drawings, an adjustable-length clamp (not shown) can also be used that can accommodate container 12 of varying lengths. Such a clamp (not shown) is also designed to be used with the cap 30 and multi-aliquot container 12 shown in FIG. 1. The clamp (not shown) includes an upper center section from which a radially extending upper arm extends; a lower center section from which a radially extending lower arm extends; and a position fixing means for fixedly positioning the upper and lower center sections with respect to each other. The position fixing means fixedly positions the upper arm and the lower arm with respect to each other to achieve a center section (and hence a clamp) having the desired length necessary to: (1) grip both the top cap and the bottom end of the container or the top and bottom caps of the container; and (2) exert an axially inwardly directed force against the cap(s) to maintain a vapor-tight seal between the cap(s) and the open end(s) of the multi-aliquot container.

Figure 4:
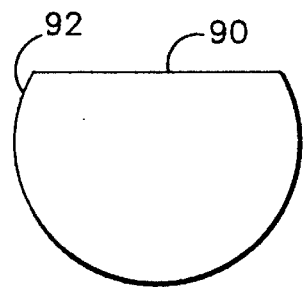
FIG. 4 shows a top view of a cross-section of an aliquot container.

FIG. 4 shows a cross-section of the multi-aliquot container 12 along a line IV—IV shown in FIG. 1. The cross-section of the container 12 shows a generally circular section 92 and a flat face 90. The flat face 90 can be used to more easily record identifying information concerning the stored sample on the exterior of the multi-aliquot container 12. The information can be recorded by writing, with a bar code or by other means. The recorded information can include relevant patient data and can provide positive specimen identification.

Figures 5, 8:
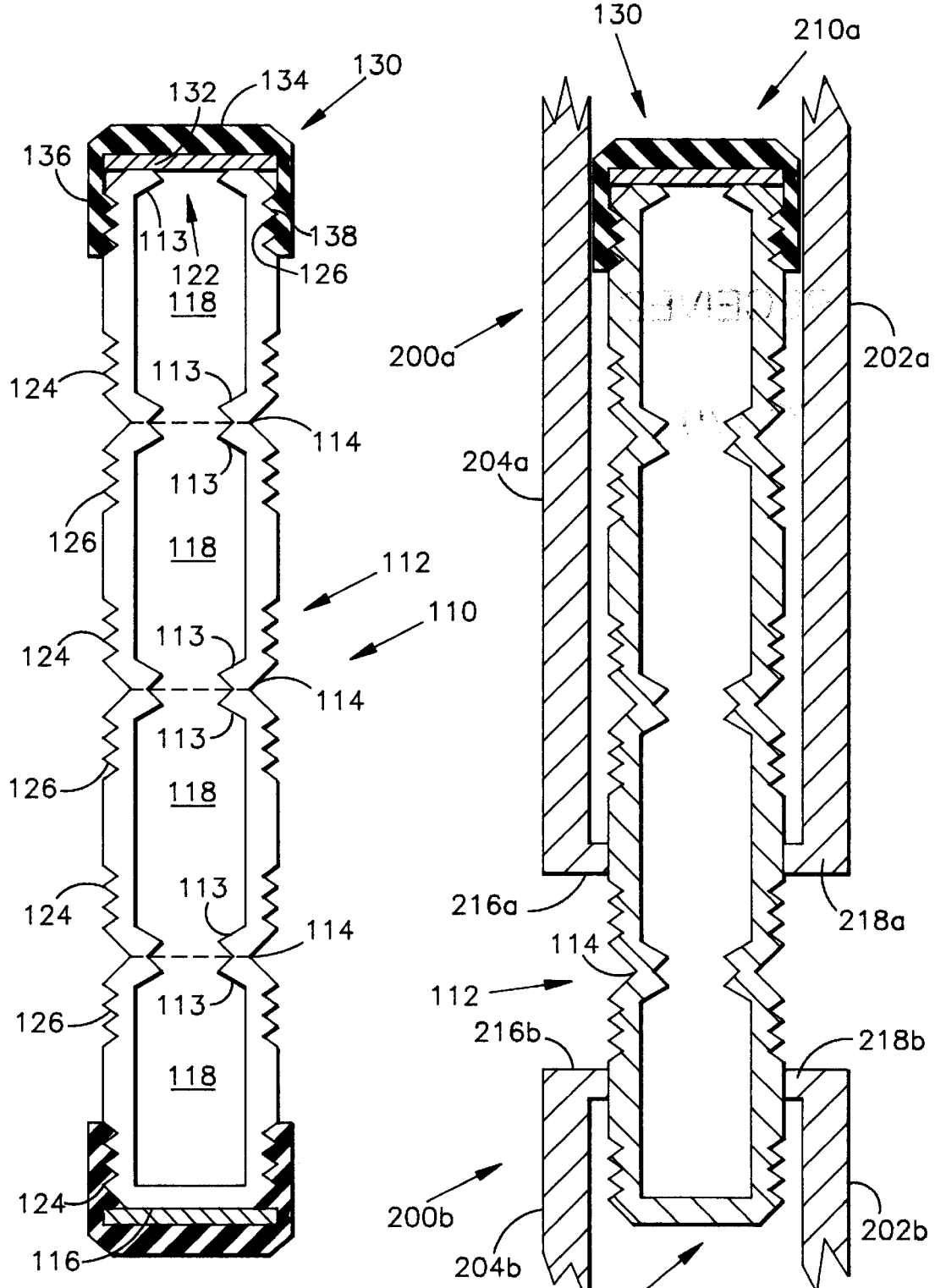
FIG. 5 shows a side, sectional view of an aliquot storage vessel with a screw cap.
FIG. 8 shows a cross-section of a pair of break tools in position to break a multi-aliquot container at a breakpoint.

FIG. 5 shows an alternate embodiment aliquot storage vessel 110 that includes a multi-aliquot container 112 and a cap 130. In this embodiment, the cap 130 is threadedly engaged onto the multi-aliquot container 112 to provide a vapor tight seal between the cap 130 and the multi-aliquot container 112.

The multi-aliquot container 112 has a bottom end 116 and an open top end 122. A plurality of spaced break-points 114 are formed to extend perimetrally around the container 112 about an axis defined by the longitudinal axis of the container 112. The breakpoints 114 are positioned at evenly spaced intervals. The breakpoints 114 separate the multi-aliquot container 112 into individual aliquots 118 which can be separated from the remainder of the sample as needed. The interior of the breakpoint 114 has protrusions 113 which contribute to breakage at the breakpoint 114 and also prevent the frozen sample in the aliquots 118 from sliding when the container 112 is broken at the breakpoint 114. The multi-aliquot container 112 is designed so that a gentle, radially directed manual force. will break the multi-aliquot container 112 and the frozen sample inside the multi-aliquot container 112 at the breakpoint 114 around which the manual force is applied, leaving a generally planar surface on the end of each portion formerly connected at the breakpoint 114. Along the length of the multi-aliquot container 112 for each aliquot 118 the exterior surface of the multi-aliquot container 112 includes a lower set of screw threads 124 and an upper set of screw threads 126.

The cap 130 includes a generally planar top surface 134, an axially extending perimetral lip 136 and a sealing member 132. The lip 136 extends axially from the perimeter of the top surface 134, and the radially inwardly facing interior surface of the lip 136 includes a set of screw threads 138 designed to matingly engage either the upper or lower set of screw threads 124, 126 of any aliquot 118 of the multi-aliquot container 112. The radially outwardly facing exterior surface of the lip 136 can be formed to comprise a plurality of flat surfaces, e.g. hexagonal shaped, to enable the user to better grip the cap 130 with a hand or tool when screwing or unscrewing the cap 130 onto or off of the multi-aliquot container 112.

The sealing member 132 is attached to the axially inwardly facing surface of the cap 130, or the axially outwardly facing edge of the container 112 which defines the open end 122, so that the perimeter of the sealing member 132 is surrounded by the radially inwardly facing surface of the lip 136 having the set of screw threads 138. When the cap 130 is attached to the multi-aliquot container 112, the top surface 134 of the cap 130 covers the open-end 122 of the multi-aliquot container 112, the set of screw threads 138 of the cap 130 are engaged with the upper set of screw threads 126 of the multi-aliquot container 112, the lip 136 of the cap 130 surrounds the perimeter of the multi-aliquot container 112 near the open end 122, and the sealing member 132 contacts the top edge of the open end 122 of the multi-aliquot container 112. The sealing member 132 is made of a pliable, generally vapor impermeable material that provides a vapor tight seal of the stored and frozen specimen, even when the top of the frozen specimen includes ridges due to a prior separation of an aliquot 118 from the multi-aliquot container 112. The compressive force due to the tightening of the cap 130 onto the multi-aliquot container 112 compresses the sealing member 132 of the cap 130 to form a vapor tight seal at the open end 122 of the multi-aliquot container 112.

The multi-aliquot container 112 and the cap 130 should be made of materials that can withstand deep freezing. Some preferred materials include polypropylene, polystyrene and polycarbonate. The volume and number of individual aliquots 118 formed in the multi-aliquot storage vessel 112 basically has no theoretical limitation, although practical limitations on the size of the container 112 may exist. External factors, such as the size of the freezer compartment in which the container is to be stored, may limit the length and/or diameter of the container 112, and hence the volume and/or size of the individual aliquots. It has been found that five aliquot vessels 11 having individual aliquot volumes of between about 0.5 and 4.0 milliliters are preferred for clinical and chemical use.

Each aliquot 118 of the multi-aliquot storage vessel 112 has an upper set of screw threads 126 and a lower set of screw threads 124. When the multi-aliquot container 112 is divided to leave an open end at both the top and bottom ends of a portion of the multi-aliquot container 112, the use of an upper and lower set of screw threads 126, 124 permits a cap 130 to be attached to both the top and bottom ends of the multi-aliquot container 112. In this case, a first cap 130 is attached to the top open end of the multi-aliquot container 112 so that the screw threads 138 of the cap 130 engage the upper set of screw threads 126 formed on radially outwardly facing surface adjacent to the top open end of the multi-aliquot container 112 to form a vapor tight seal. A second cap 130 is attached to the bottom open end of the multi-aliquot container 112 such that the screw threads 138 of the cap 130 engage the lower set of screw threads 124 at the bottom open end of the multi-aliquot container 112 to form a vapor tight seal. Note that, as shown in FIG. 5, the aliquot 118 at the bottom 116 only requires an upper set of screw threads 126 because the integrally formed bottom 116 provides a vapor tight seal without a cap 130.

The plurality of breakpoints 114 divide the multi-aliquot container 112 into a plurality of aliquots 118. The vessel of FIG. 5 is shown with four aliquots 118. However a multi-aliquot container according to the present invention could be divided into more or less aliquots 118 as the particular application or convenience requires. Each aliquot 118 is defined by either: (1) two breakpoints 114 (middle aliquot); (2) a breakpoint 114 and an open end of the multi-aliquot container (top or bottom aliquot); or (3) a breakpoint 114 and the bottom 116 of the multi-aliquot container (bottom aliquot).

When a sample is collected, it is deposited into the interior of a multi-aliquot container 112. A cap 130 is then placed over the open end 122 of the multi-aliquot container 112 such that screw threads 138 of the cap 130 and the upper screw threads 126 of the top-most aliquot 118 are threadedly engaged. The cap 130 is then screwed onto the container 112 to provide the necessary compressive force on the sealing member 132 between the cap 130 and the container 112 such that a vapor tight seal is formed at the open end 122 of the multi-aliquot container 112.

Identifying information can be recorded on the exterior of the multi-aliquot container 112 to assist in later retrieval of the desired sample. The container 112 can have a cross-section shaped as shown in FIG. 4 between the upper and lower screw threads 124, 126 for the recording of relevant patient data and/or to provide positive specimen identification. The collected sample is then frozen in the multi-aliquot storage vessel 112 by placing the storage vessel in a suitable container or cryogenic freezer, and stored in the freezer until it is needed.

When a portion of the sample is needed, the proper multi-aliquot storage vessel 112 is retrieved from the freezer. Depending on the amount of the sample that is needed, the multi-aliquot container 112 is broken at one of the breakpoints 114 to provide the technician with the number of aliquots 118 necessary to yield the appropriate amount of sample material. The multi-aliquot storage container 112 can be broken manually or with a break tool. For example, if the technician has a five aliquot container 112 and requires a quantity of sample that is equal to the amount of the sample contained in two aliquots 118, then the multi-aliquot container 112 would be broken at the second breakpoint 114 below the cap 130. The cap 130 is then removed from the two aliquot portion of the multi-aliquot container 112 and then threadedly engaged with the top screw threads 126 of the open end of the remaining three aliquot portions of the multi-aliquot container 112. The protrusions 113 prevent the frozen sample from sliding out of the container at the broken breakpoint 114. The two aliquot 118 portion can then be thawed or used as needed. The remainder of the multi-aliquot container 112 can then be returned to freezer storage. Thus, the necessary two aliquot specimen is obtained while the sample remains in the frozen state and the remaining portion of the sample can be returned to storage without having to be thawed.

Having screw threads at both the top and bottom of each aliquot 118 enables the multi-aliquot container 112 with both an open top end and an open bottom end to have a vapor tight seal at both ends through the use of two caps 130, one at each open end of the multi-aliquot container 112. This allows division of the collected sample for use or storage at different locations without having to thaw any portion of the sample. For example, if the user has a multi-aliquot storage vessel 110 with five aliquots 118 and needs to use two aliquots 118, the portions can be separated and stored without either portion being thawed. The multi-aliquot storage vessel 110 having five aliquots 118 and a first cap 130 would be retrieved. The multi-aliquot container 112 could be broken using a break tool at the second breakpoint 114 below the first cap 130. A second cap 130 would be screwed on the upper set of threads 126 at the top of the three aliquot portion of the multi-aliquot container 112 to provide a vapor tight seal. A third cap 130 would be screwed on the lower set of threads 124 at the bottom of the two aliquot portion of the multi-aliquot container 112 to provide a vapor tight seal. Thus, the necessary two aliquot specimen is obtained without having to thaw either portion of the sample.

A break tool 200 shown in FIG. 6 can be used to assist in breaking the multi-aliquot container 12, 112 at the desired breakpoint 14, 114. The break tool 200 includes an upper section 202 and a lower section 204 which pivotally rotate about a hinge 206. The proximal end of the upper and lower sections 202, 204 form a handle 208 which the user can grip when breaking the container 12, 112. The distal ends of the upper and lower sections 202, 204 form a container insertion end 218 which includes three container ports: a first container insertion port 210, a second container insertion port 220 and a third container insertion port 230. Each container insertion port has a different diameter to support the breaking of containers 12, 112 with different diameters. The container insertion end 218 could have more or less container insertion ports as desired.

FIG. 7 shows the break tool 200 in the open position. For each container port there is an upper container receiving half and a lower container receiving half. The first container port 210 includes a first upper container receiving half 212 with a first upper lip 218, and a first lower container receiving half 214 with a first lower lip 216. The second container port 220 includes a second upper container receiving half 222 with a second upper lip 228, and a second lower container receiving half 224 with a second lower lip 226. The third container port 230 includes a third upper container receiving half 232 with a third upper lip 238, and a third lower container receiving half 234 with a third lower lip 236. The upper section 202 and lower section 204 of the break tool 200 rotate about the hinge 206 so that the break tool 200 can pivot between the closed position shown in FIG. 6 and the open position shown in FIG. 7. The upper and lower lips of each container port are designed to grip the container 12, 112 while the interior of the container port is large enough to accommodate a cap 30, 130 sealing the end of the container 12, 112.

FIG. 8 shows a cross section of the first container port 210a of the break tool 200a and the first container port 210b of a substantially identical second break tool 200b with a multi-aliquot container 112 in position to be broken at the bottom breakpoint 114. The upper half 202a and the lower half 204a of the break tool 200a are closed such that the cap 130 and a portion of the container 112 are contained in the first container port 210a. The lower lip 216a and the upper lip 218a of the first container port 210a engage the sides of the container 112 above the breakpoint 114 at which the container 112 is to be broken. The upper half 202b and the lower half 204b of the second break tool 200b are closed such that a portion of the container 112 is contained in the first container port 210b. The lower lip 216b and the upper lip 218b of the first container port 210b engage the sides of the container 112 below the breakpoint 114 at which the container 112 is to be broken. By exerting opposing forces on the break tool 200a and the break tool 200b, the user can break the container 112 at the break point 114 that is between the portion of the container 112 in the break tool 200a and the portion of the container 112 in the break tool 200b.

The break tool 200 should be made of a hard, durable material that can withstand cold temperatures and also withstand the pressures exerted on the tool when it is being used to break a container 12, 112. As such, the break tool is preferably made of a material which is more durable than the material from which the container 12, 112 is made. Some suitable materials are polycarbonate (PC), polymethylmethacrylate (PMMA), and stainless steel.

When a sample is collected it is deposited into a multi-aliquot container 112 and a cap 130 is placed over the open end 122 of the multi-aliquot container 112. Identifying information can be recorded on the flat 90 of the exterior of the multi-aliquot container 112 to assist in later retrieval of the desired sample. The collected sample is then frozen in the multi-aliquot storage vessel 110 and stored until it is needed. When a portion of the sample is needed, the proper multi-aliquot storage vessel 110 is retrieved. Although a multi-aliquot storage vessel 110 having more or less aliquots 118 can be used, for purposes of example, the four aliquot storage vessel 110 of FIG. 5 is discussed here.

When a specimen is needed, the desired multi-aliquot storage vessel 112 is retrieved. Depending on the amount of the sample that is needed, the multi-aliquot container 112 is broken at one of the breakpoints 114, to provide the necessary number of aliquots 118. The multi-aliquot storage container 112 can be broken manually or using a break tool 200. For example, if the amount of the sample contained in two aliquots 118 is needed, then the multi-aliquot container 112 shown in FIG. 5 would be broken at the second breakpoint 114 below the cap 130. If the upper two aliquot portion is to be used, then the cap 130 can be removed from the upper two aliquot portion of the multi-aliquot container 112 and placed on the open end of the lower two aliquot portion of the multi-aliquot container 112 that remains after the top two aliquots are removed. Alternatively, a new cap 130 can be used. If the both two aliquot portions are to remain frozen, then a second cap 130 would be screwed on the lower threads 124 of the upper two aliquot portion and a third cap 130 would be screwed on the upper threads 126 of the lower two aliquot portion. Either portion can remain frozen or thawed as needed. Thus, the necessary two aliquot specimen is obtained while the sample remains in the frozen state and the remaining portion of the sample can be returned to storage without having to be thawed.

The ability of the clamps and screw threads to provide the necessary compressive force when the multi-aliquot container 12, 112 has both an open top end and an open bottom end with caps 30, 130 on both ends allows division of the collected sample and storage of each divided portion without having to thaw any portion of the sample. For example, if the user has a multi-aliquot storage vessel 10 with four aliquots 18 and needs to store one aliquot 18 in another location, the portions can be separated and stored without either being thawed. The multi-aliquot storage vessel 10 shown in FIG. 1 having a first cap 30 would be retrieved and the clamp 40 removed. The multi-aliquot container 12 could be broken using a break tool 200 at the first breakpoint 14 below the first cap 30. A second cap 30 would be placed on the top of the three aliquot portion of the multi-aliquot container 12 having the bottom 16. A clamp 80 would be placed over the three aliquot portion of the multi-aliquot container 12 such that the upper protrusion 85 is inserted into the cavity 38 of the second cap 30, and the lower protrusion 87 is inserted into the cavity 20 of the bottom 16. A third cap 30 would be placed on the bottom of the one aliquot portion of the multi-aliquot container 12 having an open bottom end. A one aliquot clamp (not shown) would be placed over the one aliquot portion of the multi-aliquot container 12 such that the upper protrusion is inserted into the cavity 38 of the first cap 30 and the lower protrusion is inserted into the cavity 38 of the third cap 30. Thus, the necessary one aliquot specimen is obtained and can be stored while the entire sample, both portions, remains in the frozen state.

In general, any temperature sensitive liquid solution, emulsion, gel or suspension can be stored and processed in a multi-aliquot storage vessel 10, 110. The multi-aliquot storage vessel 10, 110 has applications in many industries, including the chemical, pharmacological, cosmetic, medical, veterinary, and food industries.

It will be understood that various modifications can be made to the apparatus disclosed in this application without changing the scope of the invention as set forth in the claims attached hereto.

What is claimed is:

1. A multi-aliquot storage vessel comprising:
   a unitary tubular container having an upper end and a lower end, said upper end of said container being an open end, the length of said container between said upper end and said lower end being continuously formed and adapted to be broken into a plurality of aliquots upon application of a radially directed force, wherein there is a breakpoint between each two of said plurality of aliquots at which said container and its contents can be divided to separate at least one of the plurality of aliquots from the remainder of the plurality of aliquots;
   a cap which is formed to be attached to said upper end of said container; and
   a sealing means cooperable with said cap for providing a seal at said upper end of said container.

2. The vessel of claim 1, wherein said sealing means includes a clamp which attaches to said lower end of said container and to said cap.

3. The vessel of claim 2, wherein said clamp includes an upper arm, a lower arm and a center section, wherein when said clamp is used to seal said vessel, said upper arm attaches to said cap and said lower arm attaches to said lower end of said container, the center section having a fixable length for permitting the upper arm and lower arm to compressively engage the respective cap and lower end of the container.

4. The vessel of claim 3, wherein said cap includes a depression, said lower end of said container includes a depression, and each of said upper and said lower arm of said clamp includes a protrusion, wherein when said clamp is used to seal said vessel, said protrusion of said upper arm attaches to said depression of said cap and said protrusion of said lower arm attaches to said depression of said lower end of said container.

5. The vessel of claim 2, wherein said clamp includes a radially extending upper arm which connects to the cap of said container, a radially extending lower arm which connects to the lower end of said container, a first longitudinal center section which extends between said radially extending upper arm and said radially extending lower arm on one side of said container, and a second longitudinal center section which extends between said radially extending upper arm and said radially extending lower arm on the opposite side of said container.

6. The vessel of claim 5, wherein said cap includes a depression, said lower end of said container includes a depression, and each of said upper and said lower radially extending arms includes a protrusion, wherein when said clamp is used to seal said vessel, said protrusion of said upper arm attaches to said depression of said cap and said protrusion of said lower arm attaches to said depression of said lower end of said container.

7. The vessel of claim 1, wherein said cap includes a lip having an internal surface and an external surface, said internal surface of said lip including a set of cap screw threads; and the external surface of each aliquot of said container closest to said upper end of said container includes a set of upper aliquot screw threads formed to mate with said cap screw threads, wherein said sealing means includes said cap screw threads and said upper aliquot screw threads.

8. The vessel of claim 7, wherein the external surface of each aliquot of said container closest to said lower end of said container includes a set of lower aliquot screw threads sized to mate with said cap screw threads.

9. The vessel of claim 7, wherein the external surface of said lip is formed to have a plurality of flat surfaces.

10. The vessel of claim 1, wherein said container includes an inwardly directed protrusion at the bottom of each aliquot adjacent to a breakpoint, and an inwardly directed protrusion at the top of each aliquot adjacent to a breakpoint.

11. A multi-aliquot storage vessel comprising:
a unitary tubular container having an upper end and a lower end, said upper end being an open end and said lower end being an open end, the length of said container between said upper end and said lower end being continuously formed and adapted to be broken into a plurality of aliquots upon application of a radially directed force, wherein a breakpoint is formed between each two of said plurality of aliquots at which said container can be divided to separate at least one of the plurality of aliquots from the remainder of the plurality of aliquots;
a first cap formed to be attachable to said upper end of said container;
a second cap formed to be attachable to said lower end of said container;
a sealing means for sealing said first cap to said upper end of said container, and sealing said second cap to said lower end of said container.

12. The vessel of claim 11, wherein said sealing means includes a clamp which attaches to said first cap and to said second cap.

13. The vessel of claim 12, wherein said clamp includes an upper arm, a lower arm and a center section extending between said upper arm and said lower arm wherein, when said clamp is used to seal said vessel, said upper arm attaches to said first cap and said lower arm attaches to said second cap.

14. The vessel of claim 13, wherein each of said first cap and said second cap includes a depression, and each of said upper and said lower arms of said clamp includes a protrusion, wherein when said clamp is used to seal said vessel, said protrusion of said upper arm attaches to said depression of said first cap and said protrusion of said lower arm attaches to said depression of said second cap.

15. The vessel of claim 12, wherein said clamp includes a radially extending upper arm which connects to said first cap, a radially extending lower arm which connects to said second cap, a first longitudinal center section which extends between said radially extending upper arm and said radially extending lower arm on one side of said container, and second longitudinal center section which extends between said radially extending upper arm and said radially extending lower arm on the opposite side of said container.

16. A multi-aliquot storage vessel comprising:
a unitary tubular container having an upper end and a lower end and a longitudinal axis extending between said upper end and said lower end, said upper end being an open end and said lower end being an open end, the length of said container between said upper end and said lower end being continuously formed and adapted to be broken into a plurality of aliquots upon application of a radially directed force, wherein there is a breakpoint between each two of said plurality of aliquots at which said container can be divided along the longitudinal axis to separate at least one of the plorality of aliquots from the remainder of the plurality of aliquots, the external surface of each aliquot of said container closest to said upper end of said container including a set of upper aliquot screw threads and the external surface of each aliquot of said container closest to said lower end of said container including a set of lower aliquot screw threads;
a first cap and a second cap, each of said first and second caps including a lip having an internal surface and an external surface, said internal surface of said lip including a set of cap screw threads formed to mate with said upper aliquot screw threads and said lower aliquot screw threads;
wherein said first cap is screwed onto said upper aliquot screw threads at said upper end of said container and said second cap is screwed onto said lower aliquot screw threads at said lower end of said container.

17. The vessel of claim 16, wherein the external surface of said lip of each of said first and second caps is formed to have a plurality of flat surfaces.

18. The vessel of claim 16, wherein said container includes an inwardly directed protrusion at the bottom of each aliquot adjacent to a breakpoint, and an inwardly directed protrusion at the top of each aliquot adjacent to a breakpoint.

19. A multi-aliquot storage vessel for containing a sample material, the vessel comprising:
(1) a unitary tubular container having
    (a) a continuously formed sidewall having an exterior surface and an interior surface,
    (b) an open upper end and an open lower end,
    (c) a longitudinal axis extending between the upper end and the lower end,
    (d) a plurality of perimetrical notches formed on the exterior surface of the sidewall each of the notches being disposed in a different plane generally normal to the longitudinal axis, the notches defining a series of breakpoints at which the container can be broken into a plurality of aliquots through the application of a force directed generally perpendicular to the longitudinal axis of the container, each of the aliquots for holding a portion of a sample material, (e) each of the aliquots including an upper end and a lower end, (f) a set of upper aliquot threads formed on the external surface of the container adjacent to the upper end of each aliquot, and a set of lower aliquot threads formed on the external surface of the container adjacent to the lower end of each aliquot;

(2) a first cap and a second cap, each of the first and second caps including an end portion and a perimetrical lip, the perimetral lip including a set of screw threads sized for threadedly receiving the upper aliquot threads and lower aliquot threads;

wherein the first cap is threadedly engaged with the upper aliquot threads of the aliquot at the upper end of the container and the second cap is threadedly engaged with the lower aliquot threads of the aliquot at the lower end of the container.

20. A multi-aliquot storage system comprising:

a multi-aliquot storage vessel having a unitary tubular container, a cap and a sealing means, said container having an upper end and a lower end, the upper end of said container being an open end, the length of said container between said upper end and said lower end being continuously formed and adapted to be broken into a plurality of aliquots upon application of a radially directed force, wherein there is a breakpoint between each two of said plurality of aliquots at which said container can be divided to separate at least one of the plurality of aliquots from the remainder of the plurality of aliquots;

said cap being formed to be attached to said open end of said container; and said sealing means forming a vapor tight seal between said open end of said container and said cap; and a break tool for dividing said container at one of said breakpoints.

21. The multi-aliquot storage system of claim 20 wherein the break tool comprises an upper component having a distal end and a proximal end;

a lower component having a distal end and a proximal end;

a hinge connecting the proximal end of said upper component and the proximal end of said lower component so that said upper component and said lower component pivotably rotate about said hinge between an open position and a closed position;

the distal end of said upper component having an upper container receiving portion, the distal end of said lower component having a lower container insertion portion, said upper and lower container insertion portions forming a container insertion port in which said container can be inserted when said break tool is in said open position and in which said container can be held when said break tool is in said closed position.

* * * * *